(12) United States Patent
Hjertman et al.

(10) Patent No.: US 7,164,133 B2
(45) Date of Patent: Jan. 16, 2007

(54) DELIVERY DEVICE AND METHOD FOR ITS OPERATION

(75) Inventors: Birger Hjertman, Vällingby (SE); Gunnar Pettersson, Åkersberga (SE); Bohdan Pavlu, Nacka (SE); Anders Holte, Täby (SE); Per Hammargren, Täby (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 11/042,755

(22) Filed: Jan. 25, 2005

(65) Prior Publication Data

US 2005/0151081 A1  Jul. 14, 2005

Related U.S. Application Data

(62) Division of application No. 09/839,171, filed on Apr. 23, 2001, now Pat. No. 6,858,846, which is a division of application No. 08/886,398, filed on Jul. 1, 1997, now Pat. No. 6,221,051.

(60) Provisional application No. 60/021,397, filed on Jul. 9, 1996.

(30) Foreign Application Priority Data

Jul. 1, 1996 (SE) .................................. 9602610

(51) Int. Cl.
G01J 5/02 (2006.01)
A61M 5/00 (2006.01)
A61M 5/19 (2006.01)
A61M 5/315 (2006.01)

(52) U.S. Cl. ................. 250/339.11; 250/271; 604/189; 604/191; 604/404

(58) Field of Classification Search ........... 250/339.11, 250/339.12, 359.1, 271, 341.1, 341.7, 341.8; 604/189, 191, 404, 181; 235/462.11
See application file for complete search history.

(56) References Cited

U.S. PATENT DOCUMENTS

| 3,662,181 | A | * | 5/1972 | Hercher et al. |
|---|---|---|---|---|
| 4,529,401 | A | | 7/1985 | Leslie et al. |
| 4,564,360 | A | | 1/1986 | Young et al. |
| 4,585,439 | A | | 4/1986 | Michel |
| 4,838,857 | A | | 6/1989 | Strowe et al. |
| 4,853,521 | A | * | 8/1989 | Claeys et al. ............... 235/375 |
| 4,924,088 | A | * | 5/1990 | Carman et al. ............. 250/271 |
| 4,950,246 | A | | 8/1990 | Muller |
| 4,968,299 | A | | 11/1990 | Ahlstrand et al. |
| 4,978,335 | A | * | 12/1990 | Arthur, III ................... 604/67 |

(Continued)

FOREIGN PATENT DOCUMENTS

EP   0 549 694   6/1995

(Continued)

*Primary Examiner*—Stephone B. Allen
*Assistant Examiner*—Davienne Monbleau
(74) *Attorney, Agent, or Firm*—Dinsmore & Shohl LLP

(57) ABSTRACT

A system of marked medical containers comprises at least two containers having different properties in at least one respect, and at least one machine-readable marking on each of the containers, each marking being designed to allow discrimination between the difference in properties. Each marking allows discrimination between the difference by having at least one area with different absorbence or reflectance when irradiated with radiation in non-visible frequency ranges. A specific container comprises a syringe cartridge type container for use with a preparation delivery device.

7 Claims, 5 Drawing Sheets

U.S. PATENT DOCUMENTS

| | | | |
|---|---|---|---|
| 4,985,015 A * | 1/1991 | Obermann et al. | 604/67 |
| 5,078,683 A * | 1/1992 | Sancoff et al. | 604/67 |
| 5,318,521 A * | 6/1994 | Slettenmark | 604/67 |
| 5,360,410 A | 11/1994 | Wacks | |
| 5,383,851 A | 1/1995 | McKinnon, Jr. et al. | |
| 5,399,163 A | 3/1995 | Peterson et al. | |
| 5,480,381 A | 1/1996 | Weston | |
| 5,501,673 A | 3/1996 | Hjertman et al. | |
| 5,520,639 A | 5/1996 | Peterson et al. | |
| 5,523,560 A * | 6/1996 | Manique et al. | 250/223 B |
| 5,535,746 A | 7/1996 | Hoover et al. | |
| 5,593,390 A * | 1/1997 | Castellano et al. | 604/207 |
| 5,651,775 A * | 7/1997 | Walker et al. | 604/207 |
| 5,750,998 A * | 5/1998 | Goldman | 250/343 |
| 5,763,891 A * | 6/1998 | Yoshinaga et al. | 250/459.1 |
| 5,806,519 A * | 9/1998 | Evans et al. | 600/431 |
| 6,303,929 B1 * | 10/2001 | Oshima et al. | 250/271 |

FOREIGN PATENT DOCUMENTS

| | | |
|---|---|---|
| EP | 0549694 | 6/1995 |
| WO | WO 88/09187 | 12/1988 |
| WO | WO8809187 | 12/1988 |
| WO | WO 92/04926 | 4/1992 |
| WO | WO9204926 | 4/1992 |
| WO | WO 94/24263 | 10/1994 |
| WO | WO9424263 | 10/1994 |
| WO | WO 95/11051 | 4/1995 |
| WO | WO9511051 | 4/1995 |

* cited by examiner

DELIVERY DEVICE AND METHOD FOR ITS OPERATION

RELATED APPLICATIONS

The present application is a divisional of U.S. application Ser. No. 09/839,171 filed Apr. 23, 2001 now U.S. Pat. No. 6,858,846 which was a divisional of application Ser. No. 08/886,398 filed Jul. 1, 1997, now U.S. Pat. No. 6,221,051, which claimed the benefit of U.S. Application Ser. No. 60/021,397 filed Jul. 9, 1996.

TECHNICAL FIELD

The present invention relates to a preparation delivery device comprising a) a container for the preparation having or being prepared for the arrangement of an opening, b) a mechanism operable to deliver at least part of the preparation in the container through the opening, c) attachment means for connection of the container to the mechanism and d) a sensor system arranged to detect at least one predetermined property of the container or its content. The invention also relates to an operation method for such a device, to containers or container system for use in the device and a marking system or analyzing device relating to components of the device.

BACKGROUND OF THE INVENTION

Injection devices based on a separate delivery mechanism attachable to replaceable containers have found widespread use in many areas, such as medical delivery systems, owing to the flexibility and economy contained in the possibility of providing a reusable pump type device with more or less advanced machinery for preparing, dosing, controlling and monitoring the injection procedure whereas the replaceable container features can be limited to those necessary for safe confinement and simple expulsion of the pharmaceutical, features which furthermore may be adapted to each individual preparation type.

Delivery devices are known for use in more permanent set-ups, e.g. for hospital treatment situations, where there are few design restrictions and the pump part can be highly sophisticated in view of motorized manipulation means, processor controlled operation and data collection as well as possible interfacing against other available instrumentation. Often the design freedom is also utilized to make the pump part compatible with one or several existing or standardized cartridge, syringe or injection device types, hereby increasing the application range for the instrument and reducing adaptation costs for the cartridge part.

For ambulatory purposes the design limitations are more severe, especially for self-contained devices without connectable support. Size and weight restrictions place limitations on the number and sophistication degree of functions possible to include. Automation as an alternative measure for increasing safety and avoiding misuse is similarly restricted by the added motorized means and operation repertoire by limited capacity of energy storage means. Although handy and portable injectors may be devised with the minimum of support features necessary to safely control all the abovesaid requirements and problems in the hands of a skilled operator, a general trend in long-term medication is to place the administration responsibility on the patient himself, also in the case of child or disabled persons, e.g. by use of pen-type injectors. A high degree of automation and control is then desirable to avoid mistakes, not only at the mere injections steps but also the critical initiation and preparation steps. Patients dependent on daily administrations also have a legitimate need for convenience and devices discrete enough to be brought around in daily life. The contradictory requirements on highly sophisticated and yet small and convenient devices need to be met by new technology.

Delivery devices both for permanent and ambulatory use need a reliable sensor system for container control and verification in broad sense. The mere range of container types attachable to the general purpose pumps for stationary use in itself creates a control problem and for portable devices the option of patient self-administration require a fail-safe control and the widespread distribution of pumps and containers corresponding precautions against intended or unintended misuse or abuse. The reliance on automation for most functions in the devices assumes an input to the processor of for example the presence of container, check of its condition, verification of its non-used status and information of container type, content, concentration, expire date etc. It may also be desirable to input individual patient data and administration schemes. Even when the pump device is intended only for a single or a few container types or contents the pump should be inoperable but with these containers, also when intentional efforts are made to circumvent the safety systems. It is clear that the desirable controls may be of quite varying nature. Pure information may be transferred from a machine readable marking on the container to the device, which information may be totally unrelated to the container as in the case of patient data or a security code or related thereto as in the case of markings representing container preparation type and volume. Control of physical container characteristics, such as size and orientation, and functional properties, such as presence of preparation and plunger position, may require a non-standard design of the container with special features for sensing, a highly sophisticated all purpose monitoring system or multiple specialized sensors for each feature to be detected, all of which alternatives are incompatible with the abovesaid general demands placed on stationary or portable pump systems.

Common information carrying marking techniques are not suitable for the purposes outlined. The patent specifications U.S. Pat. No. 4,978,335 and WO 93/02720 suggest among other the use of a bar code and a bar code reader for similar purposes. Bar codes do not carry much information on a given surface, require a reader of significant size which can not conveniently be housed in small devices, utilizes a complex radiation systems and the code as such is easily manipulated and hence not safe against forgery. Finally the system is not usable for sensing any other container characteristic than the specified coding. Similar disadvantages and restrictions are present with marking systems based on reading of alphanumeric characters, magnetic strips etc.

Sensors for physical or functional container properties seem to be scarce in the prior art. Systems based on switches, as represented by U.S. Pat. No. 4,838,857, activated by a container when in proper position, give a highly inflexible sensing system unless a multitude of switches are arranged and a system susceptible to wear and contamination. Also systems based on interlocking of mating structures, as exemplified by EP 549 694, are inflexible, unprecise and easily cheated and, to the extent special key features are provided on the cartridge part, not compatible with standard containers. Known principles seem to be highly specialized, easily manipulated and not adaptable for a complementary information reading.

Accordingly there remains a need for a sensing system able to meet the various demands in especially medical delivery devices while being compatible with the typical restraints in these applications. Although the present invention has a more general utility, it will mainly be described against this background.

SUMMARY OF THE INVENTION

A main object of the present invention is to offer a sensor system limiting the above-said disadvantages with prior art suggestions. A more specific object is to offer such a system useful in medical delivery devices. Another object is to provide such a system suitable for use in portable devices by having small size, low weight and low energy consumption. A further object is to provide a reliable and not easily manipulated system. Still another object is to provide a system able to sense marked information in a reliable way. Another object is to provide a system able to sense a variety of functional properties. Yet another object is to devise a system able to sense both marked information and functional properties. A further object is to offer a sensor system being highly compatible with automation and microcontroller processing of its output.

These objects are reached with a system having the characteristics set forth in the appended claims.

By using in the system of the invention the general principle of transmitting radiation towards the object to be sensed and receiving for further analysis radiation affected by the object, several of the abovesaid objects are reached. Mechanical contact between sensor and object need not be present thereby increasing positioning and use flexibility while reducing problems with wear and contamination. Flexibility is also provided by the variety of mutual transmitter/receiver positioning possibilities available. By detecting functional object properties on the basis of a comparison between radiation received and a predetermined representation thereof, the system becomes highly flexible and adaptable to many object properties and the same receiver may be used for detection of several properties. The criteria for defining the predetermined representation may be unknown to the user and accordingly difficult to satisfy by unauthorized individuals. Use of non-imaging or even de-focused radiation has several advantages. Very simple and cheap components can be utilized. A large take up area in both width and depth facilitates positioning of the components and allows radiation received from different depths to affect the response with equal significance, of value for example with transparent objects such as in common medical containers. In sensing of functional properties this flexibility, as well as the possibility to let every interface surface affect the response, give a broad range of potentially detectable properties which may be covered by a single or a few receivers and also permit monitoring of dynamically changing properties. In sensing of marked information a large take up area may be employed to reduce misreading due to contamination, increase information amount by using multiple analog response levels in addition to structures in the marking and strongly improve security by using marking features not readily detectable by visual inspection. The latter point may be further improved on by using radiation in non-visible frequency ranges. It is clear that the same system can be used for sensing both functional properties and marked information, typically needed in medical delivery applications, and being highly beneficial where size, weight, economy and energy consumption matters, as in portable articles. Adaptation to automation is simple owing to the few components necessary, the simple driving thereof, the compatibility with scanning actions or dynamic operations and the easy processing also in real time of a sequential output from the receiver.

Further objects and advantages will become evident from the detailed description of the invention hereinbelow.

DETAILED DESCRIPTION

General

As used herein "system" shall be understood to refer to the invention generally, when including its parts, such as devices, methods of operation, marking principles and crucial component such as pump parts and containers.

As indicated in the introduction the sensor system and marking principles thereof described herein may be used for a variety of purposes within and beyond the medical area and for any type of preparations, such as chemicals, compositions or mixtures, in any container and delivered for any purpose. For reasons outlined the system has certain special values in connection with medical delivery devices where also the design constraints are more severe than in most other applications. For convenience the invention will be described in terms of this application.

The principles of the present invention may be used for delivery devices or systems in broad terms The delivery means from the device may be an infusion channel or any conducting means such as a tube or catheter, a needle or cannula or a needle-less system based on liquid jet or a particle gun with gas propellant. The container content material shall be deliverable by use of a delivery mechanism and any material fulfilling this requirement can be used. Normally the material is a fluid and preferably a liquid, including materials behaving as liquids such as emulsions or suspensions. These observations relates to the final preparation whereas other components, notably solids, may be present before final preparation. The nature of container content shall also be understood to include medical in broad terms and to embrace for example natural components and body fluids prefilled or drawn into the container although most commonly the medical is factory prepared. The invention may assist in solving special problems in connection with sensitive compounds susceptible to degradation or denaturation under mechanical stress such as high shear forces. Compounds of high molecular weight may be of this type, high molecular weight hormones for example growth hormones or prostaglandins. The invention may also assist in solving special problems in connection with medicals requiring a preparation step immediately prior to the infusion, typically a mixing of two or more components, which all may be fluid or may include a solid as when dissolving a lyophilized powder in a solvent, such as hormones or prostaglandins.

The administration manner can also be varied within broad limits and may include entirely continuous infusion, continuous infusion with varying flow or intermittent infusions or injections with repeated either equal or varying doses. Especially when combined with automation means in a preferred way the administration manner can easily be varied by adaptations in software or similar control. In portable devices the intermittent administration is common. Similarly, although delivery devices may be contemplated also for a single dosing operation, generally they are designed for more than one or multiple individual doses for intermittent administration.

In addition to the basic functions for delivery purposes the delivery system with preference may include other valuable features such as for initiating the container and its content and provide various checks and controls of both the container and the pump part electronics and mechanics.

As mentioned in the introduction the principles of the invention may be applied to delivery devices in stationary or permanent set-ups. Due to among others the simplicity provided the invention give special advantages in delivery devices for ambulatory purposes, especially those being autonomous with on-board energy storage, motor and processor means and in particular small hand-held devices of truly portable nature.

A preferred medication delivery device can be said to generally comprise at least a container for the medication having or being prepared for the arrangement of an opening, a mechanism operable to deliver at least part of the medication in the container through the opening, attachment means for connection of the container to the mechanism and a sensor system arranged to detect at least one predetermined property of the container or its content.

The Container

The container part shall be understood in broad sense and may take a variety of forms such as any kind of tube, vessel, flexible bag, vial, ampoule, cartridge, carpoule, syringe body etc. There are some advantages in using containers that are rigid, at least at its opening or the part for attachment to the mechanism but preferably generally rigid, such as vials, ampoules or syringe bodies. There are also some advantages in employing the invention in connection with containers that are at least translucent and preferably transparent at least partially and preferably generally at the frequency of the radiation used. Common container materials such as glass or plastic can with preference be used. The container may an integral or composite structure, such as including an outer casing or any other multipart construction for closures, fixtures, protection etc., and whenever used herein "container" shall be understood to include any auxiliary part present.

The container has at least one opening through which the medication pass during the main delivery operation of the device, either from the container interior to the surrounding for e.g. administration of the medical to the patient or to the container in case of aspiration of body fluids or at preparation steps such as filling, mixing or dissolution in the container, during which operations the opening need to be present. It is possible and even in many situations preferred that certain device operations, such as label reading, container control or initiation, takes place before communication has been established and the opening requirement shall then be considered satisfied by the preparation means for creating the communication such as the presence of a removable closure or a pierceable or rupturable part on the container itself as in the case of an ampoule or bag or a specially designed part as in case of penetrable membranes or septum. All communication may take place through one opening, for example both medical passage and pressure equalization in a rigid container or by delivery from a container which is flexible or has a movable or deformable part but nothing prevents that further openings are provided for similar purposes, which can be identical to the at least one opening but which can be entirely different and for example be adapted for another purpose of e.g. infusion or syringe type with a movable wall or piston.

The container may be a simple bottle, vial or bag in case the delivery device is arranged to withdraw, continuously or intermittently, metered amounts therefrom for delivery as defined. Often, and especially in connection with self-administration, the container type is more elaborate and is commonly in the form of a cartridge, being the container part of a syringe type of delivery system, which may be still more elaborate in the case of multichamber cartridges. Cartridge type containers shall be further described as they generally require additional initiation or control steps for which the principles of the invention with preference can be exploited.

A cartridge for the present purposes may generally be said to include a vessel having a front part and a rear part defining a general cartridge axis, an outlet for the preparation arranged at the front part and at least one movable wall arranged at the rear part, a displacement of which wall causes the preparation to be moved towards or expelled through the outlet. Vessel shape and movable wall have to be mutually adapted. The vessel may be designed most freely when the wall is a flexible or oversized membrane or diaphragm able to adapt by movement or reshaping to vessel internal surfaces, in which case a fluid cushion or resilient material may be needed between the wall and piston rod to smooth out applied pressure. Preferably, however, the vessel has a substantially constant internal cross-section, with a similarly constant vessel axis, between front and rear parts giving a generally tube-shaped vessel, and most preferably the cross-section is of the common circular type giving a substantially cylindrical vessel. The movable wall is then preferably a substantially shape-permanent, although possibly elastic, body sealingly adapted to the internal vessel surface and preferably of the plunger type having sufficient length to self-stabilize against tumbling during travel along the vessel. The front part outlet may be of any known design and directed laterally for best access in certain applications, frontal but non-coaxial with vessel axis or most commonly arranged frontal and coaxial. The outlet may be integral with the vessel or in a conventional manner the cartridge front end may be provided with an attachment therefore and before connection be provided with a breakable or penetrable sealing.

Generally the described cartridges need several kinds of initiation actions, dependent on a displacement of the movable wall, to reset the device and make possible repeated and reproducible dosing meeting high precision demands. In its first movement the movable wall may need an extraordinary break-loose force after storage to overcome both internal reshaping resistance and an increased wall friction due to adherence or depletion of lubricant in contact points. Also in relation to the weaker regular injection force, elastic and inelastic deformations and tolerances have to be evened out in the movable wall, cartridge shell, outlet attachments et cetera The preparations themselves may have compressible inclusions such as gas vesicles. Deaeration and preelection is needed to remove gas in the vessel compartment and fill out spaces for example at the front sealings, outlet attachments and the interior of the outlet devices or needles.

Dual or multi chamber cartridge types are known e.g. for preparations demanding a mixing of two or more components or precursors before administration. The components are kept separated by one or more intermediate walls of different known designs, which walls divide the vessel into several chambers, sometimes placed parallel along cartridge axis but most commonly in stacked relationship along the axis. Unification of the components may take place by breaking, penetrating or opening a valve construction in the intermediate walls, for example by introducing a pin or needle through the cartridge front, through or at the rear movable wall or by means at the cartridge exterior (compare e.g. the cited WO 93/02720). In another known design the intermediate wall or walls are of the plunger type and flow communication between the chambers is accomplished by moving the plunger to a by-pass section where the interior wall has one or several enlarged sections or repeated circumferential grooves and lands in a manner allowing byflow of rear chamber content into front chamber at displacement of the rear movable wall (compare e.g. U.S. Pat. No. 4,968,299 or WO 93/20868 and WO 95/11051). The chambers may contain gas, liquid or solids. Generally at least one liquid is present. Most commonly in pharmaceutical applications only two chambers are present and typically contains one liquid and one solid, the latter being dissolved and reconstituted during the mixing operation.

Initiation of the multi-chamber type cartridges requires all the general type steps described, although in aggravated form due to the additional walls and spaces present. In order to provide for efficient mixing generally a mixing space has to be allotted in addition to the space occupied by the component volumes. Powdered components in bulk form also require the extra space contained in interstices between particles. The mixing step may produce foam or gas inclusions requiring space to settle out. Plunger type intermediate walls generally have to be displaced at least their own length to reach the non-sealing site in the by-pass. In total multichamber type cartridges require long movable wall strokes in the initiating step, both for mixing and subsequent deaeration, and benefit in a particular way from the advantages of the current invention.

Cartridge sizes may vary strongly depending on the intended application and general ranges are difficult to give. Typical sizes in the preferred self-administration application by use of portable devices are 2 to 30 mm internal diameter and preferably 3 to 20 mm.

The Mechanism

The mechanism for delivery of medical through the container opening should basically include at least one type of pumping means which may have to be selected for the special kind or container and medical used. The pumping means may include any kind of pressure source, such as mechanical or electrolytic pressure build-up, in the container and suitable valve means for control, which method can be used with virtually any kind of container and any kind of product, such as transdermal delivery of powder, as exemplified by WO 94/24263, similar delivery through liquid jets, as exemplified by WO 94/2188, or regular tube infusion, as exemplified by WO 88/09187. Any kind of container can also be used with pumps based on peristaltic action or centrifugal action, although also for general use pumps based on controlled positive displacement are preferred and especially such pumps based on a separate cylinder and piston action, as exemplified by U.S. Pat. No. 5,480,381 for liquid jet or U.S. Pat. No. 4,564,360 for a manually operated needle based device. The common syringe type container need a specialized pumping system. Either the mechanism is adapted to act on complete syringes, having their own piston rods, by engaging and axially displacing said rod, as exemplified by the initially referenced U.S. Pat. No. 4,978,335, which may be preferred when it is desired to accommodate syringes of many different types and sizes, or the mechanism has a piston rod acting more or less directly on the piston of a cartridge type container, as exemplified by WO 95/26211, EP 143.895 or EP 293.958, which can be made smaller and more adapted to portable devices. Also dual or multiple chamber cartridges can use a similar devices for its various phases, as exemplified by the initially mentioned WO 93/02720. Although the various pump mechanisms discussed may include mechanical means for affecting the medical or a piston the means, such as a piston rod, may be actuated by any known means, such as gas pressure, vacuum, hydraulics, springs or manual operation. It is preferred to actuate the pump means by electric means such as an electrical motor, indirectly or preferably directly, among others because of its ease of adaptation to an overall automated device.

The mechanism may preferably include further components. The mechanism may for example include special means for securing doses delivered, e.g. by direct metering of medical delivered, although it is generally preferred to utilize directly or indirectly the pump means for this, e.g. by monitoring axial displacement or the rotation of a piston rod axis in a manner known per se. In particular it is preferred that the mechanism includes a control system operative to perform at least part of the abovementioned administrative patterns, initiation of containers or cartridges, self-control or surveillance and possible recording of operation steps conducted. Such systems are known in the art, as exemplified by U.S. Pat. No. 4,529,401, and may be designed in a multitude of ways. For the purposes of the present invention it is preferred that the control system drives and monitors at least part of the sensor system and processes data obtained therefrom.

The Attachment Means

The minimum requirement on the attachment means is to connect the container to the mechanism in such a manner as to allow the mechanism to perform its pumping function. The nature of pump and container principle selected may determine how critical is the relative positioning between container and mechanism. Generally when the mechanism is based on a separate pump or control valve principle with a conduit to the container the relative positioning is not critical. When the container itself is a part of the pumping or dosing principle, as for syringe or cartridge type containers, when the mechanism directly act on the container the relative positioning may be highly critical with direct influence on dosing precision. In the non-critical situations it is conceivable to have the container freely or flexibly connected to the mechanism, e.g. via a tube, although preferred, at least in portable devices, to rigidly affix the container to the mechanism as well as in case of the abovesaid critical situations. If the mechanism is generally divided in a stationary parts, for example including actuating means, chassis and transmissions, and functional movable parts, for example the active part in a pump, such as a piston rod, or in a delivery controlling valve mechanism, it is preferred to affix the container relative the stationary parts, directly or indirectly, although possible to move the container towards the mechanism during delivery. A convenient way of implementing the indirect relative attachment between stationary parts and container is to provide a housing in which at least the stationary mechanism parts are enclosed in relative immobility and to which housing the container is attached. When present the housing shall be regarded as the point of reference for motions unless otherwise stated.

The abovediscussed relative positioning is valid for the phase when the mechanism delivers medication through the container opening. Under other phases the attachment means may cooperate with the mechanism to provide other functions. A preferred such function it to cause a movement of the container. Preferably the container moves at least in relation to the stationary parts of the mechanism and preferably also in relation to the housing when present. Such a movement may be used e.g. in a docking maneuver for the cartridge including for example an attraction and a locking of the container. Alternatively or in combination the container may move in relation to the movable parts of the mechanism. Such a movement can with preference be used to perform an action on the container, especially for the purpose of initiating a container or cartridge as has been described. A preferred method and device for the latter purpose is disclosed in our copending application of even date entitled "Injection device and method for its operation" included by reference herein. A further object of any of the abovesaid motions is to move the container relative the sensor system, although this can also be made by moving the sensor system relative the mechanism or the housing. Relative movement between sensors and the container will hereinafter be referred to as "scanning". Scanning may be used for various sensing purposes, to be further discussed below, such as sensor reading of information or use of the same sensor for different purposes, spatially or sequentially. In the present context shall be observed that with preference any movement for scanning purposes can be combined with movements for any of the abovesaid purposes in order to facilitate the overall device and operation, such as a parallel initiation of a cartridge and reading and checking thereof. Movement for any purpose mentioned may include both axial and rotational displacements, as understood in terms of a container of generally rotational symmetry such as a vial or cartridge. As an example, initiation or attraction may require an axial movement whereas a rotational movement can be used for locking. For scanning purposes an axial movement may serve both reading and control of functional properties along the container whereas a rotational movement may serve to read more information distributed over container mantle surface or to shift scanning purpose.

Scanning speeds can be selected freely. The sensor system is generally compatible with most speeds, even stationary readings, and speeds can with preference be adapted to the other purposes mentioned. Typically the movement take place with less than 100 cm/sec. preferably less than 10 cm/sec and most preferably less than 1 cm/sec. Suitably the speeds are above 0.1 and also over 0.5 mm/sec.

When a housing is present it may be desirable to extend the housing at least partially and preferably substantially all over the container, for example for the purpose of protecting the container, provide guiding features to stabilize it staticly or dynamically during movement thereof or in particular to arrange sensor means in case unless positioned on carriers, stationary or movable, of their own, which housing enclosure may also act to reduce stray radiation from the surroundings. Certainly the housing can be designed as a composite or unitary structure.

The nature of the physical means for actual attachment of the container to the mechanism or housing is generally not critical for the present objects and can be of any conventional or known type, such as based on friction, push lock, undercut, bayonet lock, threads or any other fit.

The Sensor System

The sensor system of the invention is based on the transmission and reception of radiation. In the preferred application the radiation is directed towards the container or any marking thereof although, as indicated, the principles may have a more general utility as an analytical systems for objects generally or a system for machine readable information generally. In terms of the preferred application the description of the sensor system will be divided in the radiation technique, the sensor applications and the signal processing.

Radiation Technique

Initially shall be noted that although the transmitter and receiver have been discussed in the present context as if discrete components, or integral components containing both at a mutual gap distance, the terminology shall be understood to include "transceivers" i.e. components performing both functions, simultaneously or interchangeably, either with the same active component performing both functions or preferably, for best adaptation, with separate components housed within the same enclosure. Transmitters, receivers and transceivers will hereinafter collectively be referred to as "active elements". All components shall be understood in broad sense and for example any component made to output a response to beam alterations shall be regarded as a receiver and any source for radiation, natural but preferably artificial, used by the receiver shall be regarded a transmitter.

Any kind of radiation which can be affected in a detectable way by the container or a marking can be used in the sensor system. Preferably the radiation is electromagnetic radiation with a suitable frequency range between ultraviolet and microwaves and most preferably in the optical and infrared regions. As earlier indicated there are security advantages in using radiation in the non-visible ranges. The transmitter may be a maser or laser, lamps or most preferably light emitting diodes (LED's) which are preferably used for the visible and most preferably the infrared frequency range, such as between 300 to 3000 nanometers or between 500 to 2000 nanometers. Good results have been obtained in the visible area as well as infrareds in 950, 870 and 875 nanometers. The receiver should be adapted to the transmitter and for the above given types the receiver may be a photoresistor or better a photodiode or phototransistor. The receiver should be adapted in frequency to the transmitter or in case of fluorescence to any frequency resulting therefrom. For both transmitter and receiver frequency adaptation can be made by selection of type, by use of optical filters or application of electronic filters. For devices not operating in the visible range is suitable to incorporate a daylight filter to remove inadvertent surrounding influence. The specific selection of components will be dependent on which imaging principle shall be used.

As used herein an "imaging" system shall be understood as a system able to reproduce an object with details in at least two dimensions, normally requiring a system able to provide a resolution of pixels, points or lines, in the object in the two dimensions, which may take lace in different ways. A "focusing" imaging method may be used in which a lens type system give a true two-dimensional reproduction of the object, which reproduction, for example imaged on a cathode ray tube or radiation sensitive semiconductor such as a Charge Coupled Device, e.g. to give a pixel map or a line by line two dimensional output for later analysis. The focusing method may efficiently use available radiation and be focused to different depth of interest. Alternatively a "sweeping" imaging method can be used in which the object is swept point by point, which may give more general depth information and a sequential output. The sweeping can take place by irradiating the object with broad angle illumination while reception is restricted to a narrow sweeping spot by shielding or lens focusing. A more preferred method is to illuminate the object by a narrow sweeping spot, either a thin parallel beam from e.g. a laser type of transmitter or a shielded or lens focused spot from a divergent radiation source, and receive radiation from the object by a receiver which can have a narrow take-up angle but preferably has wide angle reception area. In order to give the imaging result an arrangement for providing sweeping of at least the narrow spot part should be present, e.g. by moving the active element itself, its shielding or focusing part as mentioned or a separate deflecting parts such as a mirror, lens or prism.

A "non-imaging" or integrating system shall be understood as a system designed to respond with a unified or single signal to the total radiation received from an area of the object. A non-imaging principle has the advantage of a strong simplification of the sensor system, both in respect of hardware and afterprocessing. Still with the methods according to the invention the non-imaging system give adequate control results and is preferred for most of the present purposes. A non-imaging system need not have a sweeping arrangement for reconstruction of a two-dimensional image but it is preferred that the active elements, after any modification as described, give a transmission and reception respectively, which has a stable axis orientation in relation to the support for the active element. In static sensing of container position said support is fixed in relation to the container. In scanning between sensor and container as described said axis orientation may still be stable but the support and container movable in relation to each other, preferably with the sensor fixed and the container movable in relation to a housing as described. All in all a fixed arrangement of the axis orientation and the active element support in relation to the mechanism or a housing is preferred for simplest overall design.

Although a focused image can be allowed to fall on the receiver also in the non-imaging method it has little meaning as a unified response is delivered. It is generally preferred to allow "de-focused" radiation to fall on the receiver and then preferably at least the radiation from the foremost part of the object, closest to the receiver, and most preferably radiation received substantially from all depths, should be de-focused. This may require that the radiation directed towards the receiver is out-of-focus convergent, parallel or preferably divergent. It is preferred that also the transmitter gives off de-focused radiation in the sense that an area covering irradiation is used, such as a wide beam of parallel radiation, an out-of-focus convergent radiation or preferably a divergent radiation. With preference the area or angle covered by the transmitter can be larger than the area or angle covered by the receiver. In addition to a valuable simplification of the sensor system possible, the de-focused radiation method has the advantage of giving a response from a substantial space in both width and depth of the object. This principle allows the system to register a composite "fingerprint" response of the object part observed, which is not only highly unique but also highly difficult to mimic, more so if registered in the non-visible frequency range. These advantages are amplified if the area covered by the receptor is fairly large in relation to the object and if the area covered is not sharply, but softly or gradually, delimited from non-covered areas. As the object type and target part thereof may vary strongly, absolute area values are difficult to give. A suitable space angle, with any means for correction present, drawn with its vertex at receptor axis base and with its wide end covering the take-up area, can be for example be above 10, preferably above 30 and most preferably above 45 degrees. The angle may be very large but is generally less than 180 degrees, preferably less than 160 and most preferably less than 140 degrees. The take-up area is commonly and preferably circular but when not, these values relates to a circular area of the same size as the actual.

Selection of hardware depends on which of the above sensor system principles is chosen. As indicated a sweeping spot can be obtained by a shielded divergent source, better by a lens system or a laser type device. A parallel beam can be obtained by a collimator lens system or a laser type device. A divergent beam can be obtained with a plain diffuse transmitter for simplicity or a lens system for best control. Similarly the receiver reception angle can be adjusted by shielding but better by a lens system for control and energy efficiency.

Between transmission and reception the radiation shall be affected by the object, which can take place in a multitude of ways. Generally the phenomena at play are reflection, transmission, absorption and scattering. For example, radiation meeting a change in refractive index for the radiation frequency used will be reflected to a higher or lower extent. The reflection may be diffuse if irregularities are present or may otherwise preserve a wave front and give an imaging mirror type of reflection. Radiation not reflected may be transmitted through the surface and possibly refracted. Passage may then cause absorption, roughly exponential energy fall off with transmission length, which absorption like the reflection may be diffuse when irregularities are present or otherwise imaging. Scattering may be caused by diffuse reflection and transmission.

The degree to which these phenomena affects the radiation may be strongly frequency dependent, which can be used to amplify desirable differences. In principle this can be done at two extremes. Either a narrow bandwidth or even a monochrome radiation is selected at the frequency maximizing the effect desired. A narrow bandwidth can be obtained by filtering out, through absorption or refraction, a single frequency from a basically broadband radiation source, by use of a laser type of transmitter, by use of emission spectra bands or any other method. One advantage of narrow bandwidths is high signal to noise ratios and less influence from random background radiation. Another advantage is that either the transmitter or receiver component can be selected of simple broadband type since the output is still determined by the single common frequency. A specific advantage is that a spectroscopic analysis of for example a container content is possible, which may require measurement of more than one single frequency or tuning single frequencies over a range, such as establishing an IR spectra over the component. A further advantage is the possibility to detect a frequency change intentionally introduced for marking purposes such as a fluorescence. At the other extreme a broadband radiation can be used, preferably by selecting broadband components for both transmitter and receiver. Broadband components, such as lamps, light emitting diodes and photodiodes or phototransistors, are readily available, are cheap and are energy economic. Broadband radiation further allow more object characteristics to affect the radiation. For example an analysis corresponding to color analysis in the visible region can be conducted. In most applications a broadband approach is preferred. A suitable width is then at least a variation coefficient of 1 percent, preferably at least 5 percent and most preferably at least 10 percent, plus and minus the nominal frequency, defined at the frequency where the level has fallen to less than 30 percent of the maximum level.

The radiation may be affected by the abovedescribed phenomena at several parts of the objects. Besides an area covered by the transmitter and receptor, the influence may take place at different depth of the object, such as the two surfaces of the front container surface, the content of the container and the two surfaces of the wall of the other side of the container, possibly repeated in any casing surfaces, as well as at any crack or other irregularity in these parts. Alternatively the radiation may be blocked at a first surface by a barrier to the radiation such as metal for optical and infrared radiation. Similarly the radiation may be affected repeated reflection or repeated scattering, e.g. from the container or a surrounding housing, such as a cavity filling diffuse radiation. It is also possible to introduce active measures for creating detectable differences. For example, the housing part may be given a characteristic distinctive to the cartridge part to allow detection of container presence or a particular functional part of a container or cartridge may be marked for detection. For example, one part may be designed to reflect radiation and another part to absorb radiation. As an example, for visible or infrared electromagnetic radiation carbon black can be used for absorbency and metal or titanium oxide as reflective materials.

A further degree of freedom is the relative positioning of the active elements, both in relation to each other and the active elements in relation to the object. For the sake of description, the transmitter shall be described with reference to its main beam axis, being the central axis, symmetry axis or axis of maximum intensity as the case may be, after the beam has been given a directionality by shielding, a lens system etc. when present. Similarly the main receptor axis of the receptor shall be its central, symmetry or maximum intensity uptake axis after possible correction by shielding, lens systems etc. An axis plane shall be understood as a plane in which the axis lies. Assuming first that both the transmitter axis and the receptor axis lie in the same plane, they can form a variety of angles with each other. Both can point in substantially the same direction with substantially parallel axes, i.e. with about zero degrees angle between the axes as with a transceiver type of active element. This arrangement is advantageous when concentrating on reflected radiation from the object but can also be used for transmitted light if there is some reflection within or behind the object, e.g. by in installed mirror type surface. The active elements can be placed opposely so that the transmitter beam is directed into the receptor uptake axis, i.e. with about 180 degrees angle between the axis. This arrangement is advantageous when concentrating on radiation transmitted through the object, for example when absorption is a main parameter to be detected. The receptor can be placed anywhere between the abovesaid extremes, to form any acute or obtuse angle between 0 and 180 degrees, such as about 90 degrees, to the transmitter axis. This arrangement may be advantageous when concentrating on detection of scattered radiation from the object, for example to detect impurities or unclarity. It is possible to arrange several active elements around the circle defined by rotating the receiver axis 0 to 360 degrees in relation to the transmitter axis in the above exemplified way. For example, with one or more transmitters, it might be of interest to position one receiver at about zero degrees, one at about 180 degrees and one at about 90 degrees to obtain three signals maximizing responses for reflected, absorbed and scattered radiation respectively, which can be of interest to obtain a more detailed object fingerprint or to make possible corrections for the various response components in the radiation received, e.g. elimination of influence from scattered radiation.

It has been assumed above that both the transmitter and the receiver axes are in the same plane which is not necessary although generally optimal for strongest response. Space restrictions may require the planes to be slightly displaced although still substantially parallel. The planes may also form and angle to each other, which may be useful to utilize available space or to obtain a semi-transmitted or semi-reflected response from large object such as along a cartridge axis.

It is possible to make the active elements movable in relation to each other and provide means to perform such movements, e.g. to obtain a tomographic type scanning of the object, to allow a single active element to perform the action of several or to superpose a dynamic component to a static measurement to facilitate or improve on signal processing. In most applications it is however sufficient and preferred to arrange the active elements mutually static for simplest design. As indicated above it may also be of interest to allow for a relative movement between the active components and the object, which can be done by arranging the active elements movably in relation to the device but preferably by making the object movable in relation to the device. Scanning speeds can be selected within broad limits and for example be determined with other than sensor considerations, such as the earlier suggested for cartridge movements. It is an advantage that low speeds can be used, even zero speed in case of stationary measurements.

Sensor Applications

As indicated the sensor system can be utilized to read information generally in the form or a machine readable marking. The sensor system may also detect physical functional properties of the object observed. A marking may also serve to facilitate detection of a functional property such as a marking of a critical object position. For the purposes of the present invention the object "properties" for detection shall be understood to incorporate all these possibilities.

The nature of the information transferred by a machine readable marking system can be of any kind and is not limiting for the principles of the invention. For the preferred medical delivery device application such information may be of general nature such as security codes, patient codes, administration schemes, calibration data etc. The data may be in some way related to the container such as container type or size identification, stroke length or needle type for cartridges, content preparation type, volume and/or concentration, distribution data, batch number, storage capacity, temperature sensitivity, expire dates, classification according to official standards etc. The information may be used for a variety of purposes such as simple display of the information to the user, setting of processor parameters, basis for acceptance or rejection of attached container, enabling or disabling device operation in response to patient data and security codes, selection or downloading of administration pattern, calculation of doses etc.

In order to obtain the advantages stated in respect of marking reading it is preferred to use a non-imaging sensor system, as defined and most preferably a de-focused radiation method as defined. Preferably the receptor has a divergent take-up angle for received radiation which may have a space angle of for example between 10 and 150 degrees, better between 20 and 120 degrees and most preferably between 30 and 90 degrees. The area covered on the marking by such a reception can still be controlled by the distance between the receptor and the marking. In order to concentrate the marking area the distance typically is less than 25 mm, preferably less than 15 and most preferably less than 10 mm. A certain area size is desirable to even out fluctuations and to permit even irradiation and preferably said distance is above 0.1 mm, preferably above 1 mm and most preferably above 2 mm. The shape of the area covered by the receptor may vary due to irradiation restrictions, geometry of receptor or its shielding and any curvature of the object itself. Indicative of the absolute size of the area covered, expressed as the diameter of a circle with corresponding surface, may be between 0.1 and 20 mm, preferably between 0.5 and 15 mm and most preferably between 1 and 10 mm in diameter.

The information is carried by detectable differences in any of the possible optical properties discussed above. The area covered by the receiver will generally give a unified and accordingly integrated response and it is hence possible that the abovesaid area size covered by the receiver at any time is non-uniform, for example having a gradient but preferably then a grid or raster pattern e.g. as used in printing and graphics, although preferably the area covered is substantially uniform to the radiation used. Even if possible that the marking covers only a part of the receiver covered area it is generally preferred for strongest response that the entire area is marked.

Because of the analog response it is possible to have a multitude of detectable information levels from a single marking area. These information carrying levels may form a truly analog signal by being designed to cover a continuum of possible levels, for example to represent an equally truly analog characteristic such as container content volume or concentration, e.g. by being represented between full reflection/transmission and full absorption. It is often preferred for signal treatment reasons to design the marking system to give a multiple of discrete information level responses for simple afterprocessing, i.e. a digital system. Because of the many levels detectable such a digital system shall preferably not be binary but based on more than two different levels, preferably at least three and most preferably more than three discrete levels, for example hundreds of levels. In order to facilitate binary digital afterprocessing of the signal output, it may be beneficial to adapt the multitude of possible levels to the binary scale and to design the radiation detectable levels of the marking for example to any $2^n$ value with n larger than 1 such as 4, 8, 16, 32, 64, 128 or 256 discrete levels.

In spite of the amount of information possible to extract from a single marking area spot it may be desirable to include several such information area spots in order to again and again multiply the possible combinations. Even if it is sufficient in a specific application with the alternatives from one area it may be beneficial to include a control area, preferably with another level. Accordingly it is preferred to use more than one area. In a truly analog system design such a multitude of areas may form a continuous gradient. Preferably however the areas are separated to give a step difference when read in sequence, possibly with standard level surfaces separating each information carrying area to facilitate discrimination between areas. The individual areas in such a set may be read by a number of individual receivers although preferred to use a single receiver, or a few for control, for scanning the set of areas by relative movement according to any of the mechanisms earlier described. Scanning may take place staticly or semi-staticly by moving the receiver to an area and recording its level or preferably by continuously moving the receiver over the areas to get a dynamically changing response, or by a combination of these methods.

The marking can affect the radiation in any of the general manners described such as by differences in reflection or scattering but preferably differences in absorption is employed. It is often sufficient to use differences in the total absorption over the bandwidth used, disregarding any frequency dependence, preferably by using absorbents affecting all frequencies in the bandwidth used about equal, which allows for simplest signal processing and permit use of monochrome radiation. Alternatively or in addition absorbents altering the frequency distribution can be used to create a correspondence to colors in the visible range, which strongly increases the number of combinations. The frequency differences may by a receiver able to tune the various bandwidth frequencies or preferably by using more than one receiver sensitive in different bands. Differences in absorption can be detected in transmitted radiation, by use of pigments or preferably dyes, but are preferably detected in reflected or scattered radiation, such as by placing transmitter and receiver close the same side of the marking. Although possible to arrange the marking over some other object feature to have a combined response therefrom it is generally preferred to isolate the marking response from other influences and for example use an opaque or preferably reflecting backing behind the marking, such as a metal sheet. As mentioned a suitable pigment system in visible and infrared regions is carbon black and titanium oxide, having a fairly uniform influence over a broad frequency range. The marking may be directly applied to the object for example by spraying or painting or the marking may be indirectly applied by using a label or sticker, allowing common printing method to be used and facilitating application of backing materials.

In a medical delivery system the marking principle can for example be used to provide a set or system of at least two and preferably more containers, having different properties in at lest some respect, and providing the containers with a machine readable marking of the nature described which is designed to carry information allowing discrimination between the different container property types. The container may for example be different in respect of preparation type, concentration, volume, size, cartridge diameter, security code, expire dates etc. Generally the marking would allow machine identification of container type for any purpose, such as for rejecting containers with passed expire dates, making the connection between a specific security code and a specific patient or machine screening, selection or sorting of containers for any of its properties e.g. in manufacture, distribution or stock holding. Commonly the container will also be similar in some respect, such as any of the above mentioned. Preferably the containers are similar in the respect that they are adapted for use in the same medical delivery device, such as by having similar features for connection to the attachment means, sizes adapted for use in the device and a geometry adapted for reading of its marking by the same sensor system. This will allow the device for example to reject containers not intended for use and to adapt to container types allowed.

Marked information may be brought to the device in any way, for example via a sensor arranged to receive such information specifically from a separate information strip or via a marked dummy container. For highest security it is preferred to bring the information to the device via a marking physically attached to the container, at least if the information in any way is related to the container as described.

As said the sensor system may also be used to detect a functional property of the object. Contrary to the "marking"

dealt with above, a "functional" property shall be understood as any characteristic of an object not applied to transfer information to the device but is present for the intended operational purpose of the device or is the result of the object manufacturing or use history. In the preferred application of medical delivery devices sensing of a functional property normally serves the purpose of determining or verifying adequate status of the container to be used, e.g. to allow the control system to accept or reject the container or to adapt to its specific conditions or status or to monitor a process taking place therein. The functional property is generally a physical property of the container or its content and as such difficult to falsify. Yet for safety reasons it is important that the detection is fail-safe.

In order to establish whether or not the functional property is present at a container type object the container position is irradiated and the affected radiation is received and compared with a predetermined representation of the characteristic to be detected. Normally the container is in the container position but it might also be absent, for example when the system searches for a non-present cartridge, when a calibration signal for the position as such is to be determined or when measurement against a dummy is made. As a physical property is difficult to falsify any kind of radiation sensor system principle can be utilized. An imaging system, also in the visible range, can be utilized, for example to detect a contour part of the cartridge or a discontinuity in the container or content signaling a defect or impurity when compared with a representation of the proper condition. It is often preferred however to utilize a non-imaging system or most preferably such a system based on de-focused radiation in order to exploit the general advantages inherent therein as described, e.g. to obtain unique fingerprint of several radiation type contributions or to combine in a simple system of high security able to sense both marked information and functional properties. Although functional properties are often detected by a response dependent on radiation received from different depths, it is preferred to receive radiation from about the same response angles and areas as stated for general or marked information use, if given as the area of container part closest to the active elements.

It may also be beneficial to combine functional property sensing with a relative movement between receiver and container, for example to get the dynamic response signal earlier described, to sense in sequence both marked information and functional properties or to detect several different functional properties, or the variation of a single property, along a container, for example along the axial extension of a cartridge type container. Movement of the container may also be part of a dynamic process to be monitored by the sensor system such as an emptying, filling, dilution or dissolution process or any of the abovedescribed initiation steps for a cartridge type container. Any dynamic process can be followed either statically with container and receiver mutually fixed or dynamically with a relative motion therebetween. Below some examples of various sensing options.

A contour part of the container may be sensed to verify if a container has been inserted in the device, that it has the intended size and that it is properly positioned for example in relation to the attachment means or its preset position if movably arranged. A highly specific contour part, such as a flange or closure part may be selected if an imaging sensor system is utilized. A non-imaging system can be used to detect the relative position of the contour, which response can be highly sensitive to even small positional differences if the reception angle is small compared to the displacement to be detected and if the contour is normally located within the angle area. If several orthogonal contour lines are detected the entire container position will be well determined.

Internal features may be detected provided the container is transparent to the radiation. In particular it may be beneficial to detect a movable wall, especially a plunger in a cartridge type container, for example in order to verify a fresh container by confirming that the piston is in its start position, verify completed initiation such as reconstitution or deaeration by confirming the required displacement of the plunger or contact between plungers in multichamber systems, determining doses left in the container from a sensing of current plunger position or emptied container by verified end position. Preferably sensing can take place by the absorption of the plunger material itself, optionally modified e.g. with an added absorbent, and preferably in reflected radiation. The uptake area should be adapted to the plunger size, preferably so that it covers only a part of its axial extension making it possible to detect details thereof, such as sealing rings, even in non-imaging or de-focused radiation. With preference a cartridge for this purpose can have a plunger position exposed for sensing and a marking carrying information at another part, which marking is readable in non-imaging radiation and accordingly allows sensing for both purposes by the same system.

Also the internal container content can be sensed. Presence of a solid can be detected by its absorption or scatter and the presence of a liquid can be distinguished from a gas by the difference in refractive index, for example in transmitted radiation at an off-center line where the difference in refraction give a detectable response difference. Also impurities in an otherwise homogeneous media, e.g. liquid or gas can be detected, such as unclarities or miscolorations or gas or particle inclusions by increased scatter or total absorption change form a small uptake area. Similar methods can be used to detect deficiencies in the container walls such as cracks or deformations. Preparation type can be chemically verified by measurement at spectral wavelengths typical for the product. Marking or modifications may be used to facilitate or amplify the response at detection of functional properties. For example, instead of determining a container position on the basis of a physical structure thereof a marking or at least one or preferably several spots on the container of label may serve the purpose of defining the container orientation. Verification of container presence can similarly be done by the detection of a predetermined marking. A modification may also take the form of an attached mirror reflecting part on the container or a prism reflecting or refracting facet thereon, preferably arranged to divert transmitter radiation towards the receiver.

Although the invention has been described in relation to delivery devices it is clear that the system principles can be used for any similar or entirely different purpose. For example, the marking system has a general utility and is not restricted to marking of containers but may be used on any article or for any information transfer purpose. The sensor for reading such a marking must not be included in a delivery device but can be included in any other device or in a general purpose reader. Similarly the general principle of detecting a functional property by its radiation fingerprint need not be restricted to properties of containers but can have a general utility for other articles, e.g. to detect their presence, position, appearance structure at the surface or at depth similar to any of the abovedescribed applications, and the sensor be included in any identification system. Accordingly the system may be used as a general device or method for analysis of an object, e.g. for color analysis at any frequency range or for surface or depth structure or texture analysis of any object.

Signal Processing

Processing of the signal received from the receiver can take place in any processor located anywhere, for example to continuously or intermittently by intermediate storage transmit the signal to a remote computer for processing in real or artificial time. Preferably the signal is fed to an on-board microcontroller of the device and in most instances it is also preferred to process the signal in real time. The processing will be described in terms of these options.

The signal processing for the sensor system will be different depending on which system principle is utilized. A system based on an imaging sensor system may need a signal processing able to make a connection between receiver individual pixel responses in space or time to a specific point in space, which may require parallel processing of all pixel responses, connection of each pixel response to an absolute grid address, syncronization of line sweeping to absolute start positions etc. Signal analysis may then incorporate any known system for image analysis, e.g. by comparing the signal with a predetermined representation of the object property to be detected.

In the preferred embodiment of a non-imaging system signal processing can basically be kept very simple. The transmitter can be made give off a stable radiation and the receiver to receive part thereof. The output from the receiver may be a stable level response, such as a stable voltage, for example when the object is non-changing or when there is no relative movement between receiver and object, whereby a substantially "static" response is relied upon. The predetermined representation of the property to be identified can then similarly be a level and the process of comparison may include any algorithm for comparing the measured level with one or several predetermined levels to determine whether or not the sought property shall be deemed present. Preferably the response in measured several times or over a certain time to average out any small disturbances or variations.

A more reliable measurement can be obtained when detecting and comparing more than one part of the object, preferably parts with differences in response levels. Hereby "relative" rather than "absolute" levels can be determined by comparison which among others improve reliability. Relative measurements can be made in a "semi-static" method by making more than one static measurement on different object parts. At sensing of marked parts several markings, including separate reference levels or constituting mutual reference levels, can be read and used to establish response level differences. Similarly when sensing a functional property more than one measurement can be done at the site of interest and at another site, e.g. at plunger position and a plunger absent position or at filled and empty container parts, or at two points of different responses at the same object, e.g. at plunger sealing rings and therebetween respectively. Alternatively or in addition a relative measurement can be based on differences in radiation responses at different wavelengths, if present, at the same object area. The signal processing may here incorporate an establishment of the response difference or ratio between the sensed parts and comparison of this relative level between one or several predetermined level differences or ratios.

It is generally preferred to include a "dynamic" action to the signal, i.e. to provoke a signal changing over time and in some way record and act on the response versus time function. A dynamic response may serve to provide a relative response in the same way as the semi-static method although with more data available for elimination of random factors. A dynamic method also generally permits extraction of more information for calculation and decision making owing to the time axis present, such as rate of change or floating average or noise level calculations. Signal processing may here include comparison with a sequence of relative levels to be confirmed, possibly independent of time, or a more complete curve fit for more elaborate analysis. A dynamic response can be caused in several ways. A continuous change in sensor system frequency may cause a varying response. A monitoring of a dynamic process, such as the dissolution of a compound or the movement of a piston, can be followed over time. As indicated a preferred dynamic response is caused by a relative movement between object and sensor, which may serve both to read a sequence of markings and several different object functional parts along the movement track or several details along the same object part giving a more detailed fingerprint thereof.

The above described dynamic method, wherein receiver output is monitored for its amplitude versus time function, directly or indirectly, and the function processed before an activity is based thereon, is highly compatible with existing processor technology. The function may be obtained and treated as continuous but it is preferred that values are sampled from the device output, which may be made at irregular but preferably at regular time intervals at a certain frequency. Sampling can be in any of several known ways. The sampling may be digital in the sense that the amplitude is compared with a reference level and either set to a binary 1 or a binary 0 depending on whether the amplitude is above or below the reference level, which may be varying but preferably is fixed. Among others for extracting more information from the raw data an analog sampling method is generally preferred, in which the function absolute amplitude value is repeatedly registered. The analog value can be processed in an analog processor but it is mostly preferred to convert the value to digital form and process it in a digital processor. The signal may in a manner known per se be filtered to remove certain frequency ranges.

The signal processing may include a function comparable with automatic gain control, either by hardware or by software, meaning that system amplification at the response level of interest is adapted to the present purpose of either overview or magnification.

The function values may be memorized and processed at any time and rate but real time processing is generally preferred in most applications, which may still require some memorizing of the values to be simultaneously processed at any given time. It is preferred that the processing involves at least two, preferably three and most preferably a multiple of function values at a time.

In all of the above discussed signal processing methods it is possible to use several transmitters and receivers at a time. This may be done for any of the reasons earlier discussed, such as collection of radiation from different angles to allow calculation of a corrected response. Specifically for the now discussed objects it may be of interest in the static method to use several receivers to sense different object parts, in the relative measurement method additionally to simultaneously sense the levels on which the relative measurements are based or to collect responses at several frequencies and in the dynamic method additionally to cover several aspects of the process monitored.

In any of the methods discussed it is also preferred to modulate the transmitter signal and to detect the modulation at the receiver output signal. This in order to exclude influence from random factors and disturbances not having the modulated characteristic. A highly advanced modulation can be used although it is often sufficient to superimpose on the radiation a stable modulation frequency. Such a frequency should be clearly above the ubiquitous power line frequencies with overtones and can for example be above 0.5 kHz and preferably above 1 kHz but can be kept below 1000 kHz and preferably below 100 kHz. The receiver system should be tuned to the modulation frequency as narrow as possible, but can have a small bandwidth in case doppler shifts are to be detected. Filtering of the signal can be made with any known method based on hardware or software.

The above exemplified signal processing steps shall not exclude any other type of common processing. In particular any processing may require normal initializing steps, such as zeroing or the system by measurement of the background radiation immediately before insertion of a container or normalization against a standard dummy container or reference marking absorbency level.

DESCRIPTION OF DRAWINGS

Figure 1A:
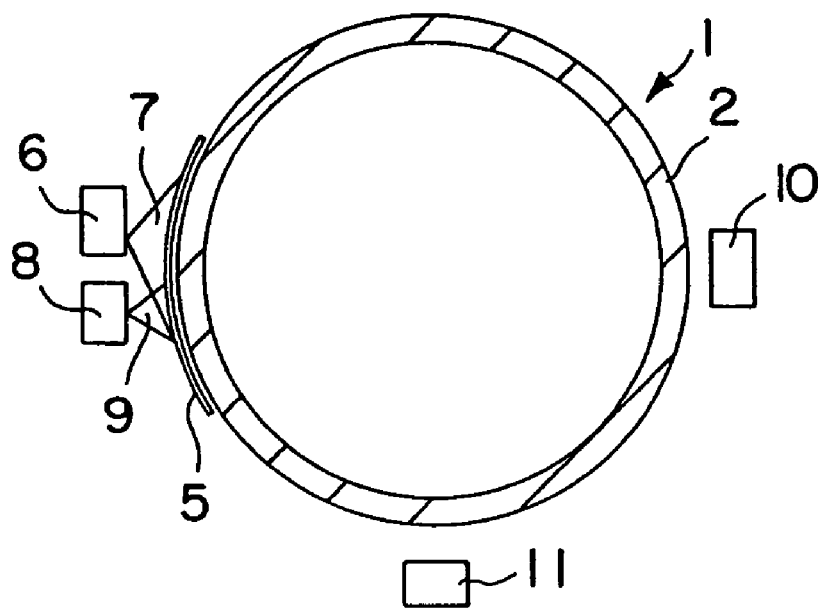
FIGS. 1a and 1b show schematically active elements arranged at a cartridge type container.
Figure 1B:
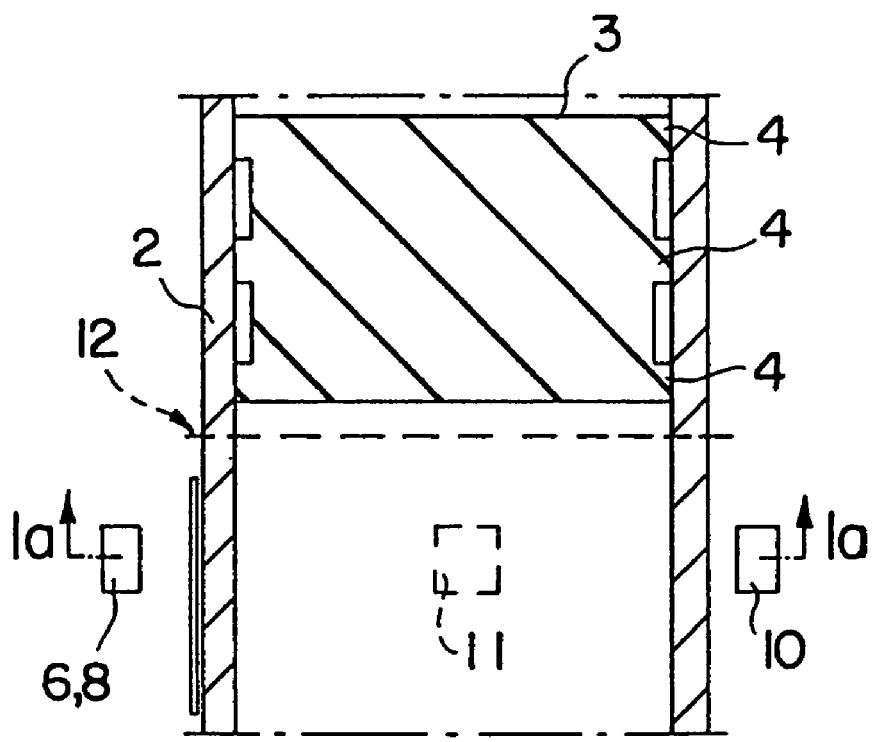

FIGS. 1a and 1b show in schematic form a cartridge type container generally designated 1 and having a cylindrical part 2 and containing a plunger 3 having three sealing rings 4. Attached to the cylindrical part 2 is a label 5 assumed to bear coded surfaces on a totally reflective backing. A transmitter is indicated at 6, giving off radiation in the form of a wide cone 7. A first receiver 8 is arranged close to transmitter 6 and facing in the same direction and which receiver collects radiation from a cone 9 which is somewhat more narrow than transmitter cone 7. A second receiver 10 is arranged, relative the transmitter 6, on the opposite side of the container and facing towards the transmitter 6. A third receiver 11 is arranged at about right angle relative the transmitter 6 axis and facing towards container interior. In the relative positions shown the transmitter 6 radiation is directed towards the label 5 and the first receiver 8 collects radiation reflected from the label part irradiated by the transmitter 6. As the label is not translucent receivers 10 and 11 do not receive any direct radiation from the transmitter 6 but may receive random radiation scattered in a housing or entered from the surroundings and their outputs may be used to correct the response from the first receiver 8 for any such background radiation. If the container is axially displaced so that the plane of active elements becomes positioned at 12, that is between label 5 and plunger 3, the response from the receivers will be entirely different. Assuming that the container 1 is transparent some radiation will be reflected at the outer and inner surfaces of the radiation entering side of the container, similar reflections will occur at the radiation exit side of the container, absorbtion will take place in the walls and possible container content and some scattering will take place at all these events. The change in output from the receivers can easily be detected, i.e. the second receiver 10 may receive considerably more radiation than when behind the label. If the container is further displaced to locate the plane of active elements at the plunger 3 the receiver signals will again change and in particular the first receiver 8 will record the typical radiation reflected from the plunger, which sensing can be static or dynamic if made during movement of the container and in the latter case the difference in response at and between the sealing rings 4 may be detected.

Figure 2:
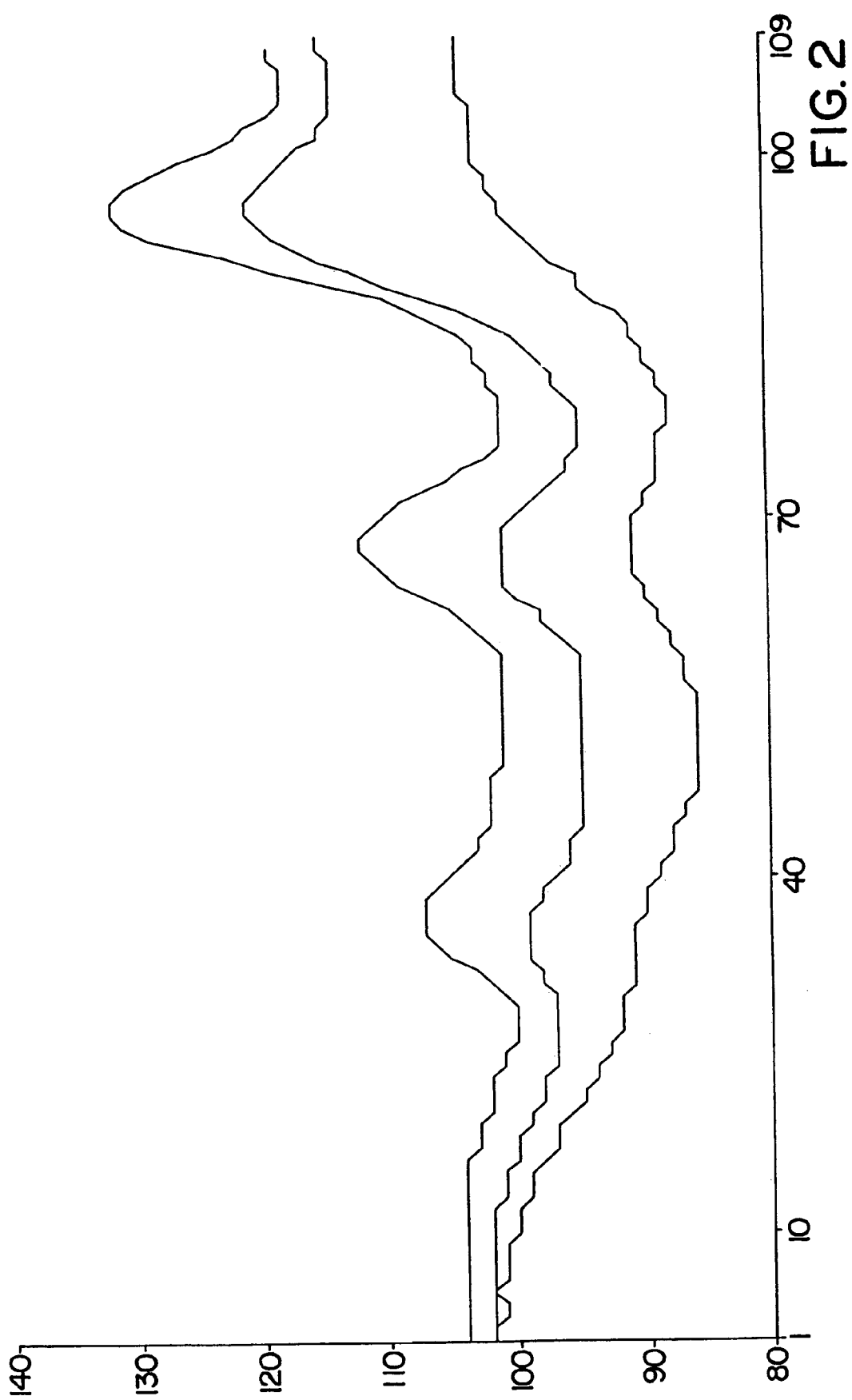
FIG. 2 is a diagram of an actual response in reflected radiation from a scanning over a plunger position.

FIG. 2 shows an actual response from a sensor system operating in the infrared region when passing over a plunger with three sealing rings inserted in a transparent syringe type container. The vertical axis gives the response level from the receiver in digitized values between 0 and 256 and the horizontal axis lengths in arbitrary units. The three curves represent the response when measured through transparent filtering labels being, from above, clear, green and blue respectively. It can be seen that the differences in response at the three sealing rings of the plunger are clearly detectable, even when the filtering label has a color closely resembling the color of the plunger material, as in the lowermost curve.

Figure 3:
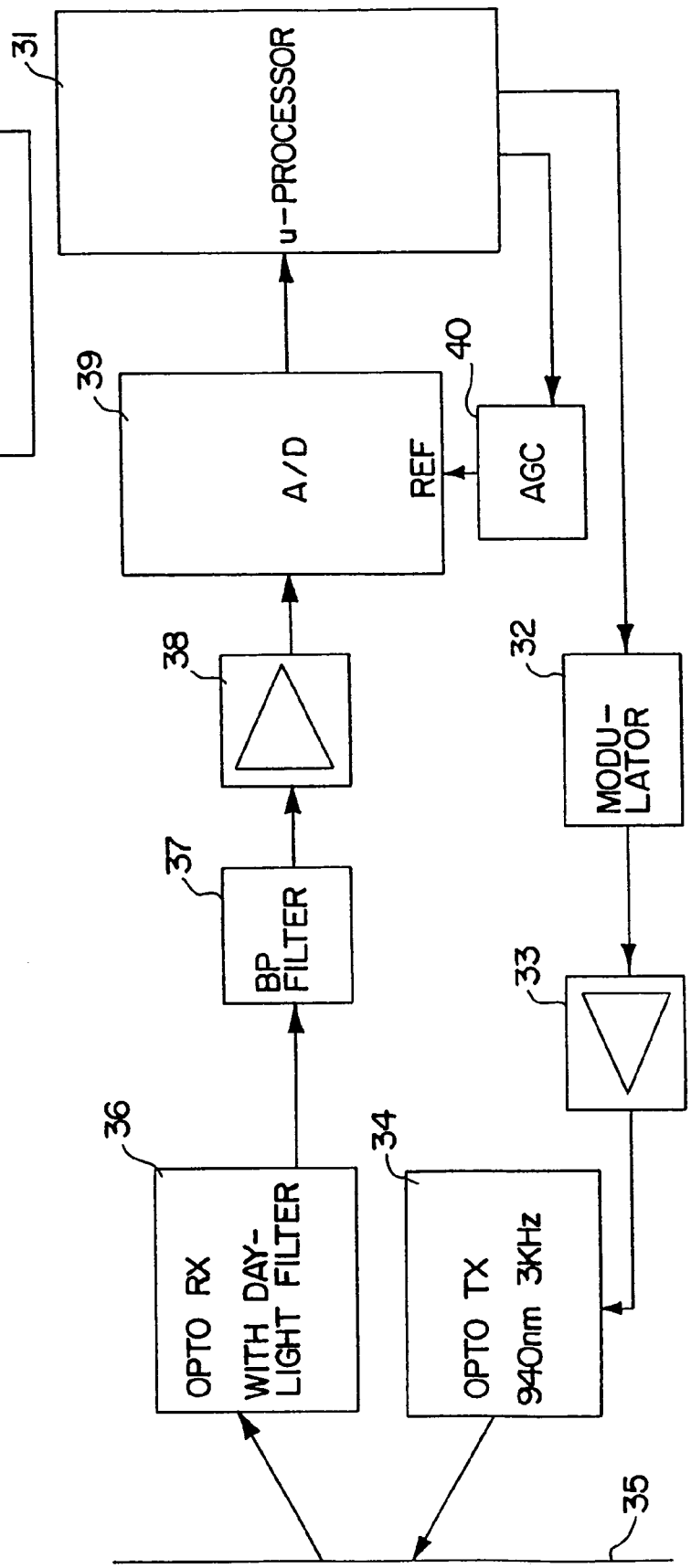
FIG. 3 is a simplified flow block diagram over suitable electronics for a sensor system according to the invention.

FIG. 3 is a block diagram over the main functions in a suitable sensor system according to the invention. A microcontroller 31 activates and deactivates the transmitter 34 over a modulator 32 and amplifier 33 to give a 3 kHz varying output from the transmitter having a nominal wavelength of 940 nm. The radiation hits and is affected by an object surface 35 and part of the radiation is collected by the receiver 36. The output signal from the receiver 36 is filtered in a bandpass filter to extract frequency components narrowly around the 3 kHz modulation frequency. This signal is amplified in 38 and fed to an A/D converter 39 and the digital output is returned to the microcontroller 31. Based on the signal received and on comparison levels of interest the microcontroller 31 may activate an automatic gain control unit (AGC) 40 to deliver a reference level to the A/D converter to permit a shift of reference level and level range resolution for the digitalization. The microcontroller may have access to software for bandpass filtering, the AGC function and for example cluster analysis for comparison of receiver response with predetermined characteristics to be identified.

Figure 4:
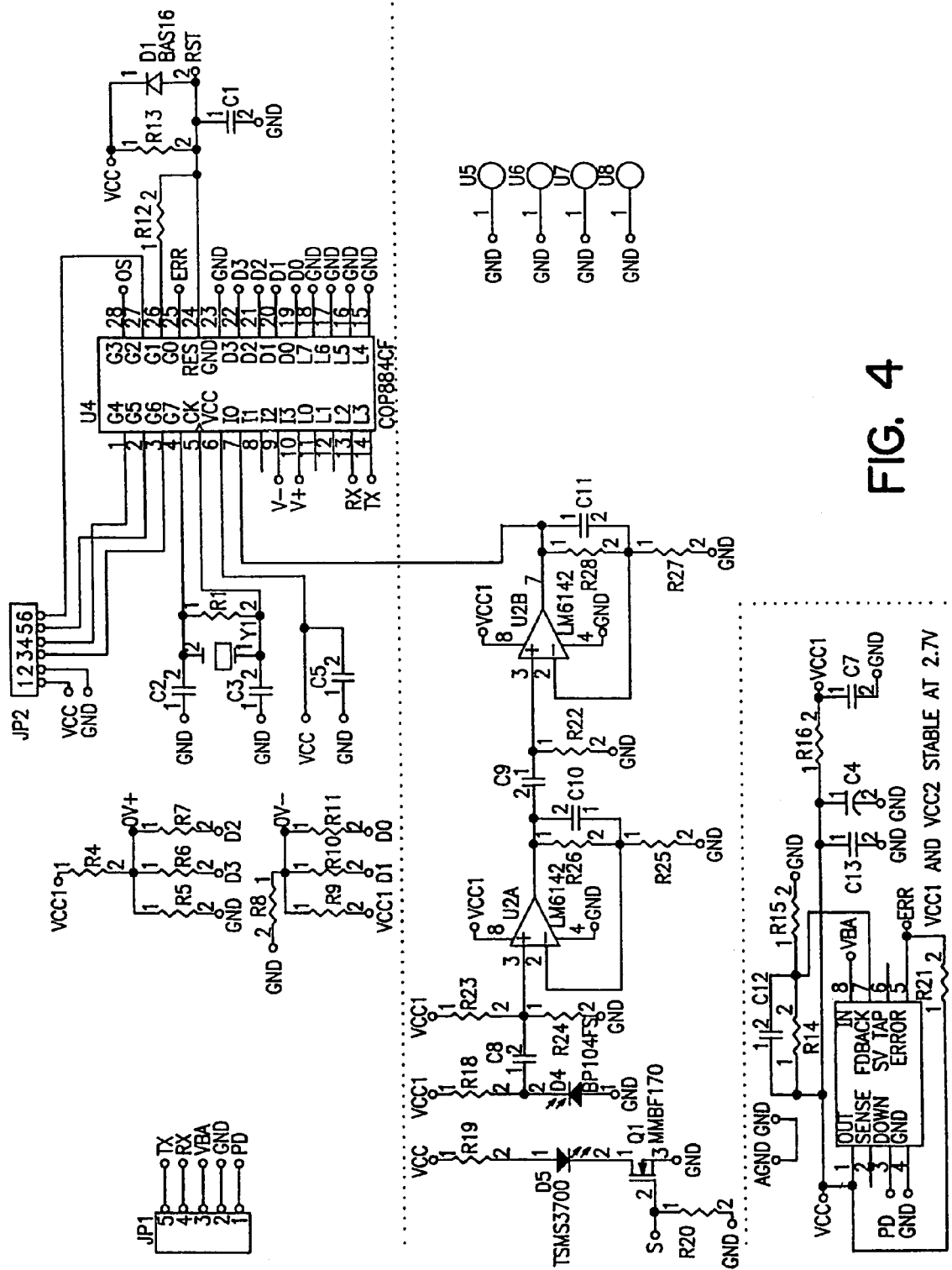
FIG. 4 is a detailed circuit diagram for use in the electronics of FIG. 3.

The circuit of FIG. 4 is basically composed of three parts, a power supply part shown at the lower section of the drawing, an analog radiation part shown in the middle section and a digital processing part shown at the top. The radiation signal for the LED transmitter is modulated from the processor U4 (pin 28, "s") via the transistor Q1 of the transmitter diode D5 (TSMS3700). The radiation from the object impinges on the photo diode receiver D4 (BP104FS) and is transformed into a current. The radiation part further comprises double filtering and amplifier steps where the filters are of bandpass type, i.e. each filter includes both a low pass and a high pass filter. The signal enters the high pass filter C8, R23, R24, is amplified in U2A and enters the low pass filter C10, R25, R26. The procedure is repeated in high pass filter C9, R22, amplifier U2B and low pass filter C11, R27, R28. After these analog steps the signal enters the A/D converter, being part of the microcontroller U4. The signal is processed in digital form in the microcontroller U4 by use of software, e.g. digital filtering, sorting and comparing algorithms etc. The resistors R4 to R11 act together with the microcontroller as an AGC function, allowing detailed analysis of different amplitude levels.

Figure 5:
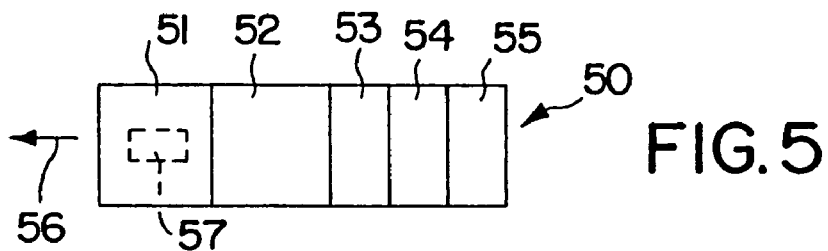
FIG. 5 is examples of labels with markings to be read by the sensor.

FIG. 5 shows a simple label with markings to be used on a cartridge type of container for example as illustrated in FIG. 6. The label 50 has a first large uniformly colored area 51 with predetermined absorption, which is intended to be read staticly, i.e. when the area is kept fixed in relation to the sensor. The absorption level of the surface may bring information about the cartridge type, content or concentration or may be used for calibration purposes. Field 52 is a window in the label which window is entirely clear and transparent and which window is intended to allow sensing of cartridge interior and especially the presence of a plunger. Fields 53, 54 and 55 are again uniformly colored areas of preferably different absorption levels which carry information of for example the same type as area 51. The window 52 and the fields 53, 54 and 55 are intended to be read dynamically in sequence under relative movement between label and sensor as indicated by arrow 56. A sensor is indicated in phantom lines at 57 in a first position over the static field 51. After reading of this field the cartridge with the label is moved in direction of arrow 56 which will cause window 52 and fields 53, 54 and 55 to pass across the sensor 57 to produce a response versus time function processable by electronics. It is assumed that all label surface except the window 52 is substantially non-transparent, by sufficient pigmentation or an opaque backing, to be unaffected by radiation from behind the label.

FIGS. 6a to 6d show schematically four operational stages of a pump part 60 and a dual-chamber type cartridge 70. The pump 60 comprises a housing 61, a piston rod type member 62 and an electromechanical unit generally designated 63 operable to actuate and control the rod to both move the cartridge 70 and expel its content. With preference these pump parts are constructed according to the above referenced co-pending application. A sensor 64 is arranged at the intended cartridge position of the pump 60. The cartridge comprises a barrel 71, an outlet 72, a rear plunger 73 and a front plunger 74. On the barrel outside is attached a label for example as described in FIG. 5.

Figure 6A:
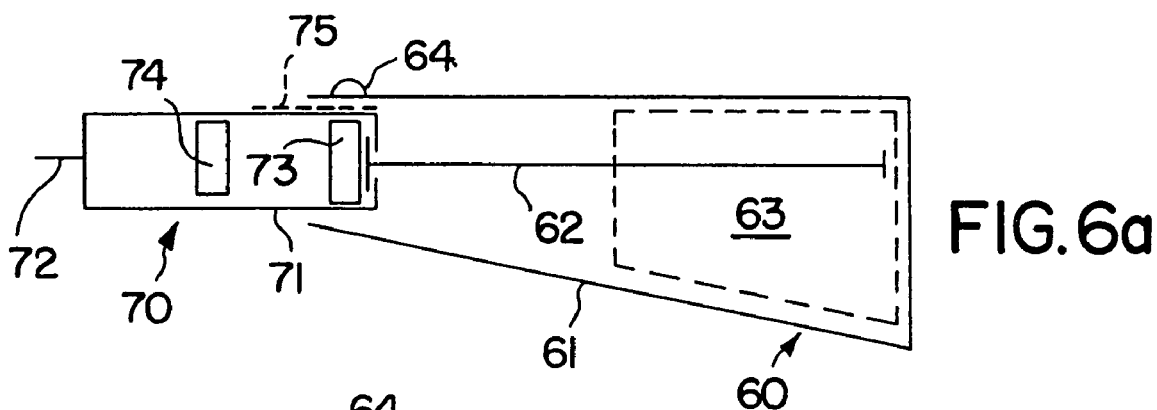
FIGS. 6a to 6d show schematically a pump device and a dual chamber cartridge in four stages of operation.

FIG. 6a shows the relative positions of pump 60 and cartridge 70 when the cartridge has just been attached to the pump with the piston rod 62 close to the rear plunger 73. The sensor 64 is located at the rear plunger 73 and over a first part of the label 75, for example the static field 51 of FIG. 5, which label part is read by the sensor 64.

Figure 6B:
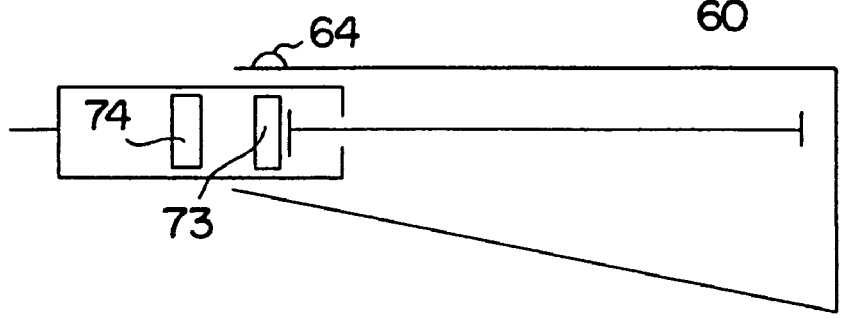

FIG. 6b shows a position in which the unit 63 has caused the cartridge 70 to move towards the pump part 60 while concurrently abutting the rear plunger 73 to maintain its absolute position. Accordingly rear plunger 73 is still at the sensor 64 but the label 75 is supposed to have traveled to a position where window 52 is between sensor 64 and plunger 73. The sensor can now verify proper plunger 73 position and characteristics through label window 52.

Figure 6C:
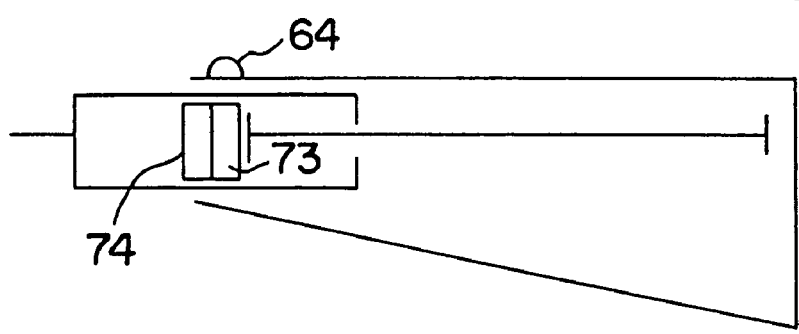

FIG. 6c shows a position when unit 62 has caused the cartridge to move still further towards the pump under movement of the plunger 73 to a position within barrel 71 where it is in contact with the front plunger 74, and perhaps the two plungers have moved a certain distance together, and the cartridge is in its final position relative the pump unit 60. Under this cartridge movement the remaining parts of label 75 have passed the sensor 64 to enable a dynamic reading of fields 53, 54 and 55 and extraction of any information encoded therein.

Figure 6D:
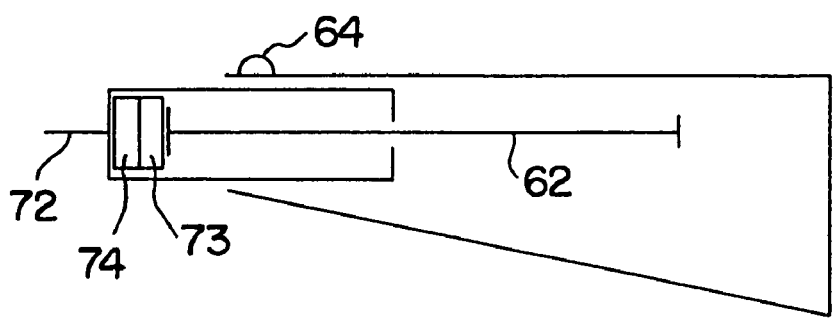

FIG. 6d shows a position wherein unit 63 has caused member 62 to move forward to expel the cartridge content in front of plunger 74 through outlet 72. Under this operation sensor 64 may monitor the disappearance of plunger 73, proper clearance of barrel 71 and detection of a marking on member 62 signaling arrival at its forward extreme position.

The exemplified embodiments are illustrative only and shall not be understood in any way limit the scope or generality of the invention as defined in the claims.

The invention claimed is:

1. A multi chamber syringe cartridge container, configured for use with a portable preparation delivery device, comprising a generally cylindrical barrel with a general symmetry axis and having a front end and a rear end, provided with an opening or a preparation for an opening at its front end; at least one displaceable piston inserted in the barrel between the front end and the rear end; and a machine readable marking on the barrel,
    wherein the marking comprises at least two marking areas with different detectable absorbency or reflectance when irradiated with radiation in non-visible frequency ranges,
    wherein the piston has at least one surface part with detectable absorbency or reflectance when irradiated with radiation in non-visible frequency ranges and said piston surface part is exposed or exposable to the radiation through at least a part of the barrel, and
    wherein at least one of said marking areas and said piston surface part are located at the same position along the barrel symmetry axis.

2. The cartridge of claim 1, wherein at least a part of the barrel along the barrel symmetry axis is free from marking, allowing exposure of the piston.

3. The cartridge of claim 1, wherein another of said marking areas is arranged along the barrel symmetry axis away from the piston position.

4. The cartridge of claim 1, wherein the cartridge is a dual chamber cartridge having two pistons.

5. The cartridge of claim 1, wherein each marking area has more than two discrete levels.

6. The cartridge of claim 1 wherein each marking area provides a step level change when the marking areas are read in sequence, statically or dynamically.

7. The system of claim 1, wherein each marking area has an opaque or reflecting backing.

* * * * *